United States Patent
Gilbert et al.

(10) Patent No.: US 12,005,042 B2
(45) Date of Patent: *Jun. 11, 2024

(54) RESCUE TREATMENT OF POST OPERATIVE NAUSEA AND VOMITING

(71) Applicant: ACACIA PHARMA LTD, Cambridge (GB)

(72) Inventors: Julian Clive Gilbert, Cambridge (GB); Robert William Gristwood, Cambridge (GB); Gabriel Fox, Cambridge (GB)

(73) Assignee: Acacia Pharma Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,032

(22) Filed: May 17, 2022

(65) Prior Publication Data

US 2023/0100786 A1 Mar. 30, 2023

Related U.S. Application Data

(63) Continuation of application No. 16/485,008, filed as application No. PCT/GB2018/050374 on Feb. 9, 2018, now Pat. No. 11,357,753.

(30) Foreign Application Priority Data

Feb. 10, 2017 (GB) .................................... 1702250

(51) Int. Cl.
| | | |
|---|---|---|
| *A61K 31/40* | (2006.01) | |
| *A61K 9/00* | (2006.01) | |
| *A61K 31/4178* | (2006.01) | |
| *A61K 31/438* | (2006.01) | |
| *A61K 31/439* | (2006.01) | |
| *A61K 31/496* | (2006.01) | |
| *A61K 31/5377* | (2006.01) | |
| *A61K 31/573* | (2006.01) | |
| *A61P 1/08* | (2006.01) | |

(52) U.S. Cl.
CPC ............ *A61K 31/40* (2013.01); *A61K 9/0019* (2013.01); *A61K 31/4178* (2013.01); *A61K 31/438* (2013.01); *A61K 31/439* (2013.01); *A61K 31/496* (2013.01); *A61K 31/5377* (2013.01); *A61K 31/573* (2013.01); *A61P 1/08* (2018.01)

(58) Field of Classification Search
CPC .................................. A61K 31/40; A61P 1/08
See application file for complete search history.

(56) References Cited

U.S. PATENT DOCUMENTS

| | | | |
|---|---|---|---|
| 4,294,828 A | 10/1981 | Thominet et al. | |
| 4,401,822 A | 8/1983 | Thominet et al. | |
| 6,169,094 B1 | 1/2001 | Perrault et al. | |
| 8,686,019 B2 | 4/2014 | Gilbert et al. | |
| 8,691,836 B2 | 4/2014 | Luehr et al. | |
| 9,084,765 B2 | 7/2015 | Gilbert et al. | |
| 9,119,836 B2 | 9/2015 | Gilbert et al. | |
| 9,545,426 B2 | 1/2017 | Gilbert et al. | |
| 9,889,118 B2 | 2/2018 | Gilbert et al. | |
| 10,085,970 B2 | 10/2018 | Gilbert et al. | |
| 10,525,033 B2 | 1/2020 | Gilbert et al. | |
| 11,357,753 B2* | 6/2022 | Gilbert ................. | A61P 1/08 |
| 2008/0188537 A1 | 8/2008 | Azorin | |
| 2009/0163544 A1 | 6/2009 | Rigby et al. | |
| 2009/0175939 A1 | 7/2009 | Bosse et al. | |
| 2011/0003005 A1 | 1/2011 | Venkatesh et al. | |
| 2013/0022688 A1* | 1/2013 | Gilbert ................. | A61P 1/00 514/397 |
| 2019/0262310 A1 | 8/2019 | Gilbert et al. | |
| 2020/0038369 A1 | 2/2020 | Gilbert et al. | |
| 2020/0093792 A1 | 3/2020 | Gilbert et al. | |
| 2021/0228543 A1 | 7/2021 | Gilbert et al. | |
| 2022/0296570 A1 | 9/2022 | Gilbert et al. | |

FOREIGN PATENT DOCUMENTS

| | | |
|---|---|---|
| DE | 102005013726 A1 | 9/2006 |
| JP | 08-507774 A | 8/1996 |
| JP | 2006-517944 A | 8/2006 |
| JP | 2009-524697 A | 7/2009 |
| JP | 2012-532194 A | 12/2012 |
| JP | 2013-511507 A | 4/2013 |
| JP | 2013-528660 A | 7/2013 |
| JP | 2016/532660 A | 10/2016 |
| WO | 2000/003740 | 1/2000 |
| WO | 03/053427 | 7/2003 |
| WO | 2006/106358 | 10/2006 |
| WO | 2007/067714 | 6/2007 |
| WO | 2007/090082 | 8/2007 |
| WO | 2007/093909 | 8/2007 |

(Continued)

OTHER PUBLICATIONS

Acacia Pharma: "Acacia Pharma Announces Positive Results from Second Pivotal Phase 3 Study of Baremsis tm (APD421) in Prevention of Post-operative Nausea & Vomiting", 8 pages, (2016), Retrieved from the Internet: URL: https: www.prnewswire.com/news-releses/acacia-pharma-annouces-positive-results-from-second-pivotal-phase-3-study-of-baremsis-apd421-in-prevention-of-post-operative-nausea-vomiting-564208971.html.

Gan T.J. et al., "Intravenous Amisulpride for the Prevention of Postoperative Nausea and Vomiting: Two Concurrent, Randomized, Double-blind, Placebo-controlled Trials", Anesthesiology, vol. 126, No. 2, pp. 268-275 (2017).

Kranke et al. I.V. APD421 (amisulpride) prevents postoperative nausea and vomiting: a randomized, double-blind, placebo-controlled, multicentre trial:, British Journal of Anaesthesia, 2013, vol. 111, No. 6, pp. 938-945.

(Continued)

*Primary Examiner* — James D. Anderson
(74) *Attorney, Agent, or Firm* — BakerHostetler

(57) ABSTRACT

Amisulpride is useful in the treatment of postoperative nausea and/or vomiting in a patient, wherein the patient has already been administered a prophylaxis drug for postoperative nausea and/or vomiting, and wherein the dose of amisulpride is 7.5 to 15 mg.

17 Claims, No Drawings

(56) References Cited

FOREIGN PATENT DOCUMENTS

| WO | 2009/126931 | 10/2009 |
| WO | 2011/110854 | 9/2011 |
| WO | 2016/162695 A1 | 10/2016 |

OTHER PUBLICATIONS

Castelli et al. "(-) S amisulpride binds with high affinity to cloned dopamine D3 and D2 receptors", European Journal of Pharmacology 432 (2001) 143-147.

Gan et al., "Consensus Guidelines for the Management of Postoperative Nausea and Vomiting", Anesthesia & Analgesia, vol. 118, No. 1, pp. 85-113, 2014.

Guslandi M. "The Clinical Use of Levosulpiride", Current Therapeutic Research, vol. 53, No. 5, pp. 484-501, 1993.

"Metoclopramide and haloperidol for the prophylaxis and treatment of nausea or vomiting induced by epidural injection of morphine for pain relief", Chinese Journal of Pain Medicine, vol. 4, No. 3, p. 167, 1998.

NCT0150704, Clinicaltrials.gov archive, History of Changes for Study: NCT01510704, Submitted Date: May 15, 2013 (v4), https://clinicaltrials.gov/ct2/history/nct01510704?V_4=View#StudyPageTop[Search Date: Jul. 28, 2021]; 9 pages.

Research progress in antiemetic drugs for chemotherapy, Journal of Shantou University Medical College, vol. 21, No. 2, pp. 123-125, 2008.

Taubel et al. "Thorough QT study of the effect of intravenous amisulpride on QTc interval in Caucasian and Japanese healthy subjects", British Journal of Clinical Pharmacology, vol. 83, pp. 339-348, 2017.

Torta et al., "Amisulpride in the short-term treatment of depressive and physical symptoms in cancer patients during chemotherapies", Support Case Cancer, No. 15, pp. 539-546, 2007.

International Search Report and Written Opinion issued in Application No. PCT/GB2017/053288 dated Jan. 23, 2018.

"Modern Surgical Anesthesia and perioperative treatment", Genetics et al. Eds. Guillin Scientific, 1st edition publication date Sep. 30, 2016 pp. 337-338.

NCT02646566, Study of APD421 as PONV Treatment (Prior Prophylaxis), 2017, Clinicaltrials.gov, 5 pages.

RN: 71675-85-9, Database Registry on STN, 1984, 1 page.
RN: 71675-90-6, Database Registry on STN, 1984, 1 page.
RN: 71675-92-8, Database Registry on STN, 1984, 1 page.

Shaikh et al., "Postoperative nausea and vomiting: A simple yet complex problem", Anesth. Essays Res., 2016, vol. 10, No. 3, pp. 388-396.

International Search Report and Written Opinion issued in Application No. PCT/GB2018/050374 dated Apr. 30, 2018.

Rosenmayr-Templeton et al., "Industry Update", Therapeutic Delivery, 2015, vol. 6, No. 2, pp. 109-114.

Gardner et al., "The broad-spectrum anti-emetic activity of the novel non-peptide tachykinin NK1 receptor antagonist GR203040", British Journal of Pharmacology, 1995, vol. 116, pp. 3158-3163.

"Dopaminergic receptors", New Pharmacology (New Yakuri-gaku) 3rd Edition, Japan, Nankodo, Nov. 25, 1996, p. 112-113.

Chen et al., "The Influence of Diphenhydramine-HC 1 (Benadryl) on Apomorphine-Induced Emesis in Dogs", Journal of Pharmacology and Experimental Therapeutics, 98 :245-250 (1950).

Cook-Sather et al., "Cisapride Does Not Prevent Postoperative Vomiting in Children", Anesth. Analg. 94.1 :50-54 (2002).

Depoortere et al., "Apomorphine-Induced Emesis in Dogs: Differential Sensitivity to Established and Novel Dopamine D2/5-HTIA Antipsychotic Compounds", Eur. J. Pharmcol. 597.1-3:34-38 (2008).

Guslandi, "Antiemetic Properties of Levo-sulpiride", Minerva Medica 81.12:855-860 (1990).

Hesketh, P.J., "Defining the Emetogenicity of Cancer Chemotherapy Regimens: Relevance to Clinical Practice", The Oncologist, 4:191-196 (1999).

Hesketh, "Chemotherapy-Induced Nausea and Vomiting", New Eng. J. Med., 358, 2482-2494 (2008).

Hirokawa et al., "Synthesis and Structure-Affinity Relationships of Novel N-(1-Ethyl-4-methylhexahydro-1.4-diazepin-6-yl)pyridine-3-carboxamides with Potent Serotonin 5-HT3 and Dopamine D2 Receptor Antagonistic Activity", Journal of Medicinal Chemistry 46(5):702-715 (2003).

Jordan et al., "Neue antiemetische Strategien-nicht nur in der Onkologie", Der Internist. 50.7:887-894 (2009) (German original and English abstract).

Kranke et al., "Intravenous Buspirone for the Prevention of Postoperative Nausea and Vomiting", Eur. J. Clin. Pharmacol. 68: 1465-1472 (2012).

Magnani, M., "Amisulpride: Pharmacological and biochemical aspects", Farmacia E Clinica, 33(3):91-97 (1994).

Makita, K., Practical Anesthesia Series "Countermeasure to PONY and Anesthesia", Anet. (quarterly journal). Maruishi Pharmaceutical, vol. 8, No. 2, pp. 18-24 (2004).

McCracken et al., "Guideline for the Management of Postoperative Nausea and Vomiting", SOGC Clinical Practice Guideline, No. 209, pp. 600-607 (2008).

Minami et al., "Role of serotonin in emesis," Folla Pharmacal., pp. 233-242, vol. 108 (1996).

Murakuni, "Mechanism of action of morphine in nausea/vomiting and countermeasures", Palliative Medicine, vol. 3, No. 1: pp. 72-78 (2001).

Pizzo et al., "Oral Cisapride for the Control of Delayed Vomiting Following High-Dose Cisplatin", Support Care Cancer, 7.1:44-46 (1999).

Porreca et al., "Nausea and Vomiting Side Effects with Opioid Analgesics During Treatment of Chronic Pain: Mechanisms, Implications, and Management Options", Pain Med. 10.4:654-662 (2009).

Puech et al., "Pharmacological Classification of Benzamides", Acta Psyhclatr. Scand. Suppl. 311:139-143 (1984).

Sulpiride, Wikipedia: The Free Encyclopedia. Wikimedia Foundation, Inc., Jun. 6, 2009. Web. Jun. 25, 2009. http://web.archive.org/web/20090729132126/http://en.wikipedia.org/wiki/Sulpiride.

Takei, D. et al., "Drug Therapy for Nausea and Vomiting", J. Pharm. Palliat. Care Sci., pp. 111-117, vol. 2 (2009).

Tonini et al., "Prevention of Radiotherapy-Induced Emesis", J. Exp. Clin. Cancer Res. 22.1:17-22 (2003) (Abstract only).

Grant et al., "Dose-ranging evaluation of the substituted benzamide dazopride when used as an antiemteic in patients receiving anticanceer chemotherapy", Cancer Chemother. Pharmacol., 1993, vol. 31, Issue 6, pp. 442-444.

International Search Report and Written Opinion issued in PCT/GB2011/050472 dated Sep. 21, 2011.

Rolla et al., "Prevention of chemotherapy- and radiotherapy-induced emesis: Results of the 2004 Perugia International Antiemetic Consensus Conference", Annals of Oncology, vol. 17, No. 1, Jan. 2006, pp. 20-28.

Spano: "Sulpride and other benzamides", Jan. 1, 1978, pp. 48-49.

International Preliminary Report on Patentability issued in PCT/GB2011/050472 dated Jun. 6, 2012.

Schoemaker et al., Neurochemical Characteristics of Amisulpride, an Atypical Dopamine D2/D3 Receptor Antagonist with Both Presynaptic and Limbic Selectivity, the Journal of Pharmacology and Experimental Therapeutics, 1996, vol. 280, No. 1, 83-97.

Lefebvre et al., "Gastric relaxation and vomiting by apomorphine, morphine and fentanyl in the conscious dog", European Journal of Pharmacology, 1981, vol. 69, pp. 139-145.

Elwood et al., "Emesis in dogs: a review", Journal of Small Animal Practice, 2010, vol. 51, pp. 4-22.

Chinese Office Action Issued in CN 201780068552.8 dated Feb. 16, 2022.

Office Action issued in JP 2019-523638 dated Aug. 25, 2021.
Office Action issued in JP 2015-187057 dated Jul. 27, 2016.
Office Action Issued in JP 2012-556586 dated Nov. 27, 2014.

Gan et al., "Fourth Consensus Guidelines for the Management of Postoperative Nausea and Vomiting", Anesth Analg, Aug. 2020, vol. 131, No. 2, pp. 411-448.

Habib et al., "Amisulpride for the Rescue Treatment of Postoperative Nausea or Vomiting in Patients Failing Prophylaxis, A Ran-

(56) References Cited

OTHER PUBLICATIONS domized, Placebo-controlled Phase III Trial", Anesthesiology, Feb. 2019, vol. 130, No. 2, pp. 203-212.

Hooper et al., "SAMBA Consensus Guidelines for the Management of Postoperative Nausea and Vomiting: An Executive Summary for Perianesthesia Nurses", Oct. 2015, vol. 30, No. 5, pp. 377-382.

Ruiz et al., "Routes of Drug Administration: Dosage, Design, and Pharmacotherapy Success", ADME Processes in Pharmaceutical Sciences, Jan. 2018, pp. 1-43.

* cited by examiner

RESCUE TREATMENT OF POST OPERATIVE NAUSEA AND VOMITING

RELATED APPLICATIONS

This application is a continuation of U.S. application Ser. No. 16/485,008, filed on Aug. 9, 2019, which is a U.S. National Phase application, filed under 35 U.S.C. § 371, of International Application No. PCT/GB2018/050374, filed on Feb. 9, 2018, which claims priority to and the benefit of GB Application 1702250.0, filed on Feb. 10, 2017, the entire contents of each of which are incorporated herein by reference in their entireties.

FIELD OF THE INVENTION

This invention relates to the use of amisulpride in the treatment of postoperative nausea and/or vomiting (PONV).

BACKGROUND OF THE INVENTION

PONV is a condition that occurs in approximately 30% of all surgical patients and 70% of high-risk patients. Risk factors for PONV include: type of surgery, sex, smoking history, prior history of PONV or motion sickness, length of surgery, use of volatile anaesthetics and opioid analgesic usage. Typically, women are more prone than men to PONV, as are non-smokers and those who have previously experienced PONV or motion sickness.

PONV is a significant issue for patients and healthcare providers. It is often rated above postoperative pain as a complication most feared by patients and thus contributes significantly to anxiety and patient distress. PONV can delay discharge of the patient from hospital or result in readmission after in-patient procedures and can require admission for ambulatory patients. This has a significant economic and social impact. With increasing rates of hospital-acquired resistant infections, it may also translate into an impact on clinical outcomes.

Numerous mechanisms have been implicated in PONV, most notably release of serotonin from the gut wall and activation of the chemoreceptor trigger zone in the brain. Consequently, several different receptors seem to be involved in PONV and represent effective targets for drug therapies. Among the most important are the serotoninergic $5HT_3$ and the dopaminergic $D_2$ and possibly $D_3$ receptors.

Despite routine use of prophylactic anti-emetics in moderate and high-risk patients, PONV still occurs in about 30-40% of cases, even in patients receiving current standard-of care of $5HT_3$ antagonists and corticosteroids and there remains a significant need for effective and safe additional agents, especially with different mechanisms of action.

The use of amisulpride as an anti-emetic is described in WO2011/110854, published on 15 Sep. 2011, which claims priority from British Patent Specification, GB 1004020.2, filed on 11 Mar. 2010. Both of these documents are incorporated into this present specification in their entirety.

In a multi-centre, double-blind, randomised, dose-ranging Phase II trial (conducted by the applicant), amisulpride was given intravenously to adult surgical patients at moderate-to-high risk of suffering PONV (prophylaxis), at doses of 1 mg, 5 mg and 20 mg, with a fourth group receiving placebo. The incidence of PONV was lower in all amisulpride groups, and significantly so in the case of 1 mg (48%, p<0.05) and 5 mg (40%, p<0.01), compared to placebo (69%). This suggests that 5 mg is at or near the bottom of a U-shaped dose response curve when evaluating the incidence of PONV.

In two multi-centre, double-blind, randomised, placebo-controlled Phase III clinical trials conducted by the applicant and involving 626 evaluable, adult surgical patients at moderate-to-high risk of suffering PONV (prophylaxis), administration of amisulpride at 5 mg successfully reduced the incidence of PONV to 48%, compared to 59% with placebo (p<0.01).

In a multi-centre, double-blind, randomised, Phase III trial involving 1147 evaluable adult surgical patients at high risk of suffering PONV (prophylaxis), again conducted by the applicant, amisulpride 5 mg in combination with a standard anti-emetic successfully reduced the incidence of PONV to 42%, compared to 53% with placebo in combination with a standard anti-emetic (p<0.001).

In another clinical trial conducted by the applicant, amisulpride at doses of 5 mg and 10 mg were compared with placebo for the treatment of PONV, in patients who had not received prior prophylaxis. There was no difference between the 5 mg and 10 mg doses in terms of clinical efficacy, suggesting that both doses are at the plateau of the U-shaped dose response curve. Both doses were significantly better than placebo at treating PONV.

SUMMARY OF THE INVENTION

The present invention is based at least in part on the results of a study of amisulpride as a rescue treatment for PONV (i.e. in patient who had received prior prophylaxis for PONV but who had subsequently suffered from PONV despite the prophylaxis), conducted by the applicant. As expected, amisulpride was found to be efficacious as a rescue treatment in PONV (following either an emetic episode and/or an episode of nausea), but upon detailed analysis of the data, it was surprisingly found that amisulpride at a dose of 10 mg was more effective as a PONV rescue treatment than amisulpride at a dose of 5 mg. This was completely unexpected, particularly given the outcome of the clinical trials described above (suggesting that there should be no difference between the two doses).

According to a first aspect, amisulpride is useful in the treatment of postoperative nausea and/or vomiting in a patient, wherein the patient has already been administered a prophylaxis drug for postoperative nausea and/or vomiting, and wherein the dose of amisulpride is 7.5 to 15 mg.

According to a second aspect, there is provided a method for treating postoperative nausea and/or vomiting in a patient, comprising administering the patient with amisulpride, wherein the patient has been administered a prophylaxis drug for postoperative nausea and/or vomiting, and wherein the dose of amisulpride is 7.5 to 15 mg.

DESCRIPTION OF THE INVENTION

Amisulpride has a single chiral centre and two enantiomers exist, i.e. (S−)-amisulpride and (R+)-amisulpride. It may be preferred to use the racemate or (S−)-amisulpride, which is substantially free of the (R+)-enantiomer. It has been reported that almost all of the therapeutic activity is to be found in the (S−)-enantiomer, and therefore use of this enantiomer means that it may be possible to reduce the dose by at least 50% (e.g., 50%, 60%, 70%, 80%, or 90%, or 50%-60%, 60%-70%, 70%-80%, or 80-90%) compared to the racemate.

A racemic mixture or racemate of amisulpride means that the amisulpride comprises both the (S−)-amisulpride and the (R+)-enantiomer. For example, the racemic mixture may comprise from 40% to 60% of (S−)-amisulpride and 60% to 40% of the (R+)-enantiomer. In some embodiments, the racemic mixture may comprise about 50% of (S−)-amisulpride and about 50% of the (R+)-enantiomer.

(S−)-amisulpride that is substantially free of the (R+)-enantiomer comprises less than 10%, less than 5%, less than 4%, less than 3%, less than 2%, or less than 1% of (R+)-enantiomer. For example, (S−)-amisulpride that is substantially free of the (R+)-enantiomer comprises less than 2% or less than 1% of (R+)-enantiomer.

As used herein, the term postoperative nausea and/or vomiting (PONV) takes its conventional meaning in the art. It is well understood in the field to mean the occurrence of one or more emetic episodes (vomiting and/or retching) or occurrence of the desire to vomit (nausea), which occurs following a surgical procedure. Retching involves the same physiological mechanisms as vomiting, but occurs against a closed glottis. PONV may be defined as nausea and/or vomiting that occurs in the 48-hour period after the end of the surgical procedure. It may be defined as nausea and/or vomiting that occurs in the 24-hour period after the end of the surgical procedure.

As used herein, an "episode of emesis" means the occurrence of an incidence of vomiting and/or an incidence of retching.

As used herein, an "an episode of nausea" means the occurrence of an incidence of nausea. This may be indicated by a patient reporting the desire to vomit or requesting an anti-emetic medication.

As used herein, a "surgical procedure" takes its conventional meaning in the art. It preferably involves the administration of a general anaesthesia e.g. general inhalation anaesthesia. The procedure may be an elective surgery (open or laparoscopic technique) under general anaesthesia. It is preferably scheduled to last at least one hour from induction of anaesthesia to extubation. Prior to extubation, a wound will be closed.

As used herein, the term "end of the surgical procedure" takes its conventional meaning in the art and is understood by the skilled person. It usually coincides with a wound closure at the end of the surgery.

As used herein, the term "about" or "approximately", when used together with a numeric value (e.g. 5, 10%, ⅓), refers to a range of numeric values that can be less or more than the number. For example, "about 5" refers to a range of numeric values that are 10%, 5%, 2%, or 1% less or more that 5, e.g. a range of 4.5 to 5.5, or 4.75 to 5.25, or 4.9 to 5.1, or 4.95 to 5.05. In some instances, "about 5" refers to a range of numeric values that are 2% or 1% less or more that 5, e.g. a range of 4.9 to 5.1 or 4.95 to 5.05.

In an aspect of the invention, the dose of amisulpride is 7.5 mg to 15 mg. Preferably, an effective amount (i.e. the dose) of amisulpride comprises 8 to 15 mg amisulpride, more preferably 8.5, 9 or 9.5 to 15 mg. The dose of amisulpride may also be 7.5 to 14.5, 14, 13.5, 13, 12.5, 12, 11.5, 11 or 10.5. Any of the aforementioned limits of the ranges may be combined with each other. Preferably, the dose is 8 to 12 mg, more preferably 9 to 12 mg and most preferably about 10 mg amisulpride. Most preferably, the dose is 10 mg. Preferably, the amisulpride is in the form of a racemic mixture.

Preferably, amisulpride is administered as a single daily dose.

Preferably, amisulpride is administered as a racemate. If it is administered as the S-enantiomer, the dose may be altered accordingly (e.g. it may be halved).

According to the invention, amisulpride is used in the "treatment" of PONV. This means that the patient is already suffering from PONV (as defined above). Also according to the invention, the patient has already been administered a prophylaxis drug for PONV. Therefore, by definition, the PONV prophylaxis has been unsuccessful.

PONV "prophylaxis" according to the invention is administered before PONV treatment. A "prophylaxis drug" means a drug that is administered with the intention/aim of preventing PONV. Suitable drugs will be known to those skilled in the art. Examples are given below.

It may be advantageous to administer amisulpride in combination with other anti-emetics (i.e. not amisulpride). The "other anti-emetic" is preferably from other class of anti-emetics, which can add additional benefits of efficacy. Therefore, preferably, the different anti-emetic agent is not a $D_2$ antagonist. These include, but are not limited to, steroids, most preferably dexamethasone, $5HT_3$ antagonists including but not limited to ondansetron, granisetron and palonosetron, and $NK_1$ antagonists such as aprepitant, netupitant or rolapitant. Amisulpride may be combined with metoclopramide, which has both $D_2$ and $5HT_3$ properties. Preferably, the other anti-emetic agent is ondansetron, granisetron or dexamethasone. Amisulpride may be combined with one or more (for example 2 or 3) different anti-emetics. Other classes of drugs may be administered via any appropriate routes of administration (e.g. via the route of administration which is typical for that drug, such as oral, intravenous or intramuscular). In some instances, other classes of drugs may be administered within 6 hours from the end of the surgery. In other instances, other classes of drugs may be administered after 6 hours from the end of the surgery.

The prophylaxis drug is preferably administered before the end of the surgical procedure. In a preferred embodiment, the prophylaxis has been administered from the period starting about 4 hours before the surgical procedure up until the time of wound closure/end of surgery. It is preferably administered no later than at the time of wound closure/end of surgery, more preferably the prophylaxis is administered at the time of anaesthesia (and more preferably, at the time of induction of the anaesthesia).

There are many prophylaxis drugs suitable for use in the invention, and these are well known to a person skilled in the art. A particular prophylaxis drug may have been chosen based on a number of different factors, such as age and weight, or whether a person is receiving certain other drugs, for example. Preferably, the prophylaxis drug is an anti-emetic drug that is not amisulpride. More preferably, the prophylaxis drug is not a dopamine-2 ($D_2$) antagonist.

In some embodiments, the prophylaxis drug is an anti-emetic selected from a $5HT_3$-antagonist, a corticosteroid, an anti-histamine ($H_1$), an anti-cholinergic, a $H_2$-antagonist or a $NK_1$-antagonist. The prophylaxis drug may be selected from any of the anti-emetic agents listed above (i.e. the combination therapies).

The $5HT_3$-antagonist may be ondansetron, granisetron, palonosetron tropisetron or dolasetron. It is preferably ondansetron, granisetron or palonosetron. More preferably, it is ondansetron. The corticosteroid may be dexamethasone, hydrocortisone, betamethasone, methylprednisolone or prednisolone. It is preferably dexamethasone. The anti-histamine ($H_1$) may be dimenhydrinate, hydroxazine, diphenhydramine, promethazine, cyclizine or meclizine. The anti-cholinergic may be scopolamine/hycosine. The $H_2$-antagonist may be famotidine. The $NK_1$-antagonist may be aprepitant. If a $D_2$-antagonist is used as the prophylaxis anti-emetic, it may be haloperidol, droperidol or domperidone.

Typical doses of the different anti-emetic agents listed above are known to a person skilled in the art. For example, ondansetron is typically in a dose of from 2 to 20 mg, or 2 to 15 mg, or about 10 mg or about 4 mg. For granisetron, the dose is typically 1-3 mg e.g. 1 mg. For dexamethasone, a typical dose is from 4-20 mg e.g. 4 mg.

Amisulpride for use according to the present invention may be packaged for sale together with accompanying instructions for use. The instructions for use (drug label) preferably specify that the patient to be treated should have undergone a surgical procedure and that they should be selected from the group of patients who have received prior prophylaxis for PONV that has been unsuccessful (i.e. rescue treatment). They also preferably specify that the dose of amisulpride is 10 mg.

Amisulpride for use in the present invention is preferably formulated as an intravenous formulation (and intended for intravenous administration). The amisulpride may be in the form of a salt, hydrate or solvate. Salts include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example, alkali metal salts such as sodium and potassium salts and alkali earth metal salts such as magnesium and calcium salts, and organic amine salts, such as morpholine, piperidine, dimethylamine and diethylamine salts.

An intravenous formulation of amisulpride for use in the invention may be in the form of a sterile injectable aqueous or non-aqueous (e.g. oleaginous) solution or suspension. The sterile injectable preparation may also be in a sterile injectable solution or suspension in a non-toxic parenterally-acceptable diluent or solvent, for example, a solution in 1,3-butanediol. Among the acceptable vehicles and solvents that may be employed are water, phosphate buffer solution, Ringer's solution and isotonic sodium chloride solution. In addition, sterile, fixed oils may be employed as a solvent or suspending medium. For this purpose, any bland fixed oil may be employed, including synthetic mono- or diglycerides. In addition, fatty acids such as oleic acid may be used in the preparation of the intravenous formulation of the invention. Suspensions may be formulated according to the known art using those suitable dispersing or wetting agents and suspending agents.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Compositions for injection are typically aqueous, and comprise a buffer, e.g. citrate buffer. No other ingredients may be required. The pH of such a composition may be, for example from 4 to 7, e.g. about 5.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

An intravenous unit dose of amisulpride suitable for use in the invention is preferably a single injection containing amisulpride. In a preferred embodiment, this could be in the form of a vial of the active agent(s) along with a syringe and needle or a prefilled syringe/needle combination.

In some embodiments, the amisulpride is in a non-IV injectable formulation. It may be in the form of a solid or liquid formulation, and may be formulated for oral administration. The solid formulations may be in the form of a tablet or capsule, a melt tablet, or in the form of a dispersible powder or granules (that may need to be added to water). Liquid formulations may be in the form of an aqueous or oily suspension or in the form of a syrup, and they may be packaged in a vial.

Amisulpride may be in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical delivery, transdermal and transmucosal patches, creams, ointments, jellies, solutions or suspensions may be employed. For sub-lingual delivery, fast dissolving tablet formulations may be used, as well as a number of the presentations described above. For oral administration, which is preferred, amisulpride may be administered as tablets, capsules or liquids.

In a preferred embodiment, an oral unit dose of amisulpride is in the form of one of more tablets, or one or more capsules. The unit doses of amisulpride may be provided in a blister pack.

Amisulpride formulations may contain any number of pharmaceutically acceptable excipients, such as sweeteners and preservatives.

Formulations of amisulpride suitable for use in the invention are described in WO2011/110854.

Where a use or a method of the invention provides for the administration of more than one drug, they can be administered simultaneous, sequentially or separately. It is not necessary that they are packed together (but this is one embodiment of the invention). It is also not necessary that they are administered at the same time. As used herein, "separate" administration means that the drugs are administered as part of the same overall dosage regimen (which could comprise a number of days), but preferably on the same day. As used herein "simultaneously" means that the drugs are to be taken together or formulated as a single composition. As used herein, "sequentially" means that the drugs are administered at about the same time, and preferably within about 1 hour of each other.

The prophylaxis drug should have been administered before an incidence of emesis has occurred. It has preferably been administered as a single prophylactic dose.

Preferably, the amisulpride is administered by IV infusion (push), preferably over a time period of from about 20 seconds up to about 20 minutes. A longer infusion time may be preferred if the patient has pain on injection, for example. In some embodiments, the amisulpride is administered over about 1 to 15, 1 to 10, 1 to 5 or 1 or 2 minutes. The amisulpride is preferably administered in a single dose.

The amisulpride should be administered as soon as is practically possible following a first emetic episode and/or following a first nausea episode (e.g. a first request for anti-emetic medication to treat nausea or a report of the desire to vomit). Preferably, the amisulpride is administered within 1 hour of a first emetic episode and/or within 1 hour of a first nausea episode. More preferably, it is administered within 30 minutes of a first emetic episode and/or within 30 minutes of a first nausea episode. More preferably still, it is administered within 15 minutes of a first emetic episode and/or within 15 minutes of a first nausea episode.

In some embodiments, no further doses of amisulpride are administered in the 24 hours following the initial dose. In some embodiments, the initial dose according to the invention is followed by at least one other dose within about 24 hours, preferably within about 12 hours, from the first dose.

In a preferred embodiment, the patient is human.

The following study illustrates the invention.

Study 1

Protocol

A randomised, double-blind, placebo-controlled study of amisulpride for IV injection as treatment of established postoperative nausea and vomiting, in patients who have had prior prophylaxis was conducted. The primary aim of the study was to compare the efficacy of 5 mg and 10 mg amisulpride to placebo as treatment of established PONV, in patients who have had prior PONV prophylaxis.

The study was performed in adult patients (≥18 years) with an expected duration of inhalational anaesthesia of at least 1 hour, who experienced PONV in the 24-hour period after surgery, having had prior PONV prophylaxis.

Amisulpride at a dose of 5 mg or 10 mg or matching placebo was given once by slow IV administration, over about 2 minutes.

The primary efficacy variable was the dichotomous variable: success or failure of initial PONV treatment, where success is defined as no emetic episodes (vomiting or retching) from 30 minutes to 24 hours after administration of study medication and no administration of antiemetic rescue medication at any time in the 24-hour period after study medication (a "complete response").

The secondary efficacy variables included:

The occurrence and severity of nausea (a VRS score>0) and of significant nausea (a VRS score≥4), including measures of the time course of nausea, such as area under the curve for nausea scores for time periods up to 24 hours.

The occurrence of vomiting (to include retching) after administration of study medication.

Use of anti-emetic rescue medication.

Time to failure of initial PONV treatment.

Sub-analyses of success and failure according to various parameters, including by time of onset of PONV relative to end of surgery and by sex.

Results

The complete response (CR) rates were as follows:

| Placebo (235 patients) | 28.5% |
| Amisulpride 5 mg (237 patients) | 33.8% (p = 0.109) |
| Amisulpride 10 mg (230 patients) | 41.7%, (p = 0.003) |

CONCLUSION

There is a benefit to administering amisulpride at a dose of 10 mg (compared to a dose of 5 mg) when it is being used as a "rescue" treatment, i.e. when it is being used to treat patients having an episode of PONV when the patient has received prior prophylaxis that has been unsuccessful. A 10 mg dose of amisulpride has been shown to be particularly effective in this circumstance. This may lead to a very helpful reduction in length of stay in the post-anaesthesia care unit and therefore may provide a benefit to the healthcare provider.

The invention claimed is:

1. A method for treating postoperative nausea and/or vomiting (PONV) in a patient, comprising administering to the patient amisulpride at a dose of 9.5 mg to 10.5 mg, wherein the patient has been administered a non-amisulpride prophylaxis drug prior to surgery, and wherein the amisulpride is administered by IV infusion over a time period of from about 20 seconds up to about 20 minutes.

2. The method of claim 1, wherein the prophylaxis drug is not a dopamine-2 ($D_2$) antagonist.

3. The method of claim 1, wherein the prophylaxis drug is an anti-emetic selected from a $5HT_3$-antagonist, a corticosteroid, an anti-histamine (H1), an anti-cholinergic, a $H_2$-antagonist and a $NK_1$-antagonist.

4. The method of claim 1, wherein the amisulpride is administered in combination with another anti-emetic, either sequentially or simultaneously.

5. The method of claim 4, wherein the another anti-emetic is a $5HT_3$ antagonist, an $NK_1$ antagonist or a steroid.

6. The method of claim 5, wherein the another anti-emetic is dexamethasone, ondansetron, granisetron, palonosetron, aprepitant, netupitant or rolapitant.

7. The method of claim 1, wherein the amisulpride is substantially in the form of a racemate.

8. The method of claim 1, wherein the amisulpride is administered within 1 hour following a first emetic episode and/or following a first nausea episode.

9. The method of claim 8, wherein the amisulpride is administered within 30 minutes following the first emetic episode and/or following the first nausea episode.

10. The method of claim 9, wherein the amisulpride is administered within 15 minutes following the first emetic episode and/or following the first nausea episode.

11. The method of claim 1, wherein the amisulpride is administered by IV infusion over about 1 to 15 minutes.

12. The method of claim 11, wherein the amisulpride is administered by IV infusion over about 1 to 10 minutes.

13. The method of claim 11, wherein the amisulpride is administered by IV infusion over about 1 to 5 minutes.

14. The method of claim 11, wherein the amisulpride is administered by IV infusion over about 1 to 2 minutes.

15. The method of claim 1, wherein the amisulpride is administered at a dose of 10 mg.

16. The method of claim 1, wherein the amisulpride is administered as a single daily dose.

17. A method for treating postoperative nausea and/or vomiting (PONV) in a patient, comprising administering to the patient racemic amisulpride at a dose of 10 mg, wherein the patient has been administered a non-amisulpride prophylaxis drug prior to surgery, and wherein the racemic amisulpride is administered by IV infusion over a time period of from about 20 seconds up to about 20 minutes.

* * * * *